United States Patent
Aufrichtig et al.

(10) Patent No.: US 6,623,161 B2
(45) Date of Patent: Sep. 23, 2003

(54) METHOD AND APPARATUS FOR IDENTIFYING AND CORRECTING LINE ARTIFACTS IN A SOLID STATE X-RAY DETECTOR

(75) Inventors: Richard Aufrichtig, Mountain View, CA (US); Paul R. Granfors, Sunnyvale, CA (US); Douglas Albagli, Clifton Park, NY (US); George E. Possin, Niskayuna, NY (US); John M. Boudry, Waukesha, WI (US)

(73) Assignee: GE Medical Systems Global Technology Company, LLC, Waukesha, WI (US)

( * ) Notice: Subject to any disclaimer, the term of this patent is extended or adjusted under 35 U.S.C. 154(b) by 5 days.

(21) Appl. No.: 09/682,386

(22) Filed: Aug. 28, 2001

(65) Prior Publication Data

US 2003/0043967 A1 Mar. 6, 2003

(51) Int. Cl.[7] .............................................. G01D 18/00
(52) U.S. Cl. ...................... 378/207; 378/98.8; 348/246; 348/247; 382/275
(58) Field of Search ................................ 378/207, 98.8, 378/62, 98.4; 250/252.1; 348/180, 246, 247; 382/275

(56) References Cited

U.S. PATENT DOCUMENTS

| | | | | |
|---|---|---|---|---|
| 4,841,555 A | | 6/1989 | Doi et al. .................. 378/98.4 |
| 4,897,788 A | | 1/1990 | King .......................... 378/12 |
| 4,996,413 A | | 2/1991 | McDaniel et al. ........ 250/208.1 |
| 5,047,863 A | | 9/1991 | Pape et al. .................. 348/247 |
| 5,272,536 A | | 12/1993 | Sudo et al. ................. 348/243 |
| 5,499,114 A | * | 3/1996 | Compton .................... 358/483 |
| 5,657,400 A | * | 8/1997 | Granfors et al. ............ 382/254 |
| 5,854,655 A | | 12/1998 | Watanabe et al. ........... 382/247 |
| 6,118,846 A | * | 9/2000 | Liu .............................. 378/62 |
| 6,381,374 B1 | * | 4/2002 | Pourjavid ................... 382/275 |
| 6,381,487 B1 | | 4/2002 | Flohr et al. ................. 600/425 |
| 6,400,798 B1 | * | 6/2002 | Leparmentier et al. ..... 378/98.8 |
| 6,404,851 B1 | * | 6/2002 | Possin et al. .............. 378/98.7 |
| 6,404,853 B1 | * | 6/2002 | Odogba et al. ............ 378/98.8 |
| 6,415,063 B1 | * | 7/2002 | Pourjavid ................... 382/275 |
| 6,418,241 B1 | * | 7/2002 | Schreiner .................... 382/263 |
| 6,453,008 B1 | * | 9/2002 | Sakaguchi et al. ......... 378/98.7 |
| 6,488,409 B1 | * | 12/2002 | Vafi et al. .................... 378/207 |
| 6,529,622 B1 | * | 3/2003 | Pourjavid ................... 382/149 |

FOREIGN PATENT DOCUMENTS

| | | |
|---|---|---|
| DE | 198 54 939 A1 | 6/2000 |
| EP | 0 962 888 A2 | 12/1999 |
| EP | 1 089 559 A2 | 4/2001 |
| JP | 10283496 | 10/1998 |

OTHER PUBLICATIONS

International Search Report—International Application No. PCT/US 02/24906, completion of search report date Nov. 25, 2002; mailing date of search report Dec. 13, 2002.

* cited by examiner

*Primary Examiner*—Drew A. Dunn
*Assistant Examiner*—Courtney Thomas
(74) *Attorney, Agent, or Firm*—McAndrews, Held & Malloy, Ltd.; Peter J. Vogel; Michael A. Dellapenna

(57) ABSTRACT

A method is provided for identifying detector elements in a solid state X-ray detector susceptible to causing line artifacts due to faulty detector elements that leak charge. A portion of the X-ray detector is covered by a radiation occluding material and the detector is exposed to a level of radiation sufficient to reach a predetermined threshold in the exposed portion of the detector. An image representative of the radiation is acquired and further analyzed to determine whether line artifacts exist. Data lines found to exhibit line artifacts are stored in the image processor.

22 Claims, 5 Drawing Sheets

METHOD AND APPARATUS FOR IDENTIFYING AND CORRECTING LINE ARTIFACTS IN A SOLID STATE X-RAY DETECTOR

BACKGROUND OF INVENTION

An embodiment of the present invention generally relates to X-ray systems utilizing a solid state multiple element X-ray detector for producing an image; and more particularly, to techniques and apparatus for identifying data lines susceptible to line artifacts and for correcting line artifacts.

Solid state X-ray detectors have been proposed that comprise a two dimensional array of 1,000 to 4,000 detector elements in each dimension (x,y). Each detector element comprises a photo detector that detects and stores charge representative of an amount of radiation incident on the detector element. Each detector element further includes a thin film transistor (TFT) connected to the photo diode and operated as a switch to enable and disable read out of the charge stored on the photo diode. Each detector element ultimately produces an electrical signal which corresponds to the brightness of a picture element in the X-ray image projected onto the detector. The signal from each detector element is read out individually and digitized for further image processing, storage and display.

One application of the solid state detector has been for thoracic imaging. During thoracic imaging, it is typical to utilize the entire detector field of view to receive the X-ray beam. The detector field of view is entirely covered by the patient during thoracic applications. Because the X-ray beam is transmitted through the body of the patient before impinging anywhere upon the detector, typically no region of the detector receives a high level of radiation.

More recently, the solid state X-ray detector has been proposed for use in general radiology applications, such as imaging an arm, knee, hand, or any other part or parts of the body that would not utilize the entire field of view. Since a smaller part of the body is being imaged, the patient does not entirely cover the detector field of view. Hence, some regions of the detector may be exposed to greater amounts of radiation than other areas. For example, if an image of a foot is taken, the foot may cover only a portion of the detector. Thus some regions of the detector may receive a relatively high level of radiation, while other regions may receive a relatively low level of radiation. In this instance, a region of the detector may be exposed to a level of radiation great enough such that the signal level is sufficient to cause the TFT to begin to conduct, or "leak", even while maintained in the OFF state. This signal level is referred to as the TFT leakage threshold. The TFT leakage threshold may not be the same for all configurations of detector elements. For example, the TFT may begin to conduct when the diode is only at one half saturation if the detector element includes a TFT and a storage capacitor, but does not include a light shield. It is also possible that the TFT may begin to conduct only if the signal level is, for example, at least five times the level necessary to saturate the diode if the detector element includes a low capacitance diode.

When a TFT begins to conduct while in the OFF state, charge on the data line may occur. Typically, detector elements are read out in rows or columns. For example, when a column of detector elements is read out, the charges stored in the detector elements within the present column are sequentially read row by row. Detector elements not presently being read are maintained OFF in order that a charge read out on a particular line may be correlated to one detector element.

However, when a TFT leaks charge while OFF, it adds charge to the output line for a column thereby causing an increased charge to be correlated to a different detector element. If the detector elements are then read in a manner such that the region that received a low level of radiation (i.e. a level of radiation below the TFT leakage threshold) is read out before the region that received a high level of radiation (i.e. a level of radiation equal to or above the TFT leakage threshold), then the TFT may begin to conduct and leak charge onto the output line even while the region that received the high level of radiation is not being read. The leakage charge adds a bias to the read out of detector elements in regions that received a low level of radiation and appears (if not corrected) as line artifacts. Hence, line artifacts may occur in the region that received a low level of radiation due to differences between leakage signals on adjacent data lines.

Methods have been proposed for identifying and correcting image artifacts that may be caused by faulty detector elements, or other anomalies present in the X-ray detector, which appear in the acquired image as bad pixels. The bad pixels are identified during the evaluation of calibration images. These calibration images may be created by exposing the detector to background radiation or to a level of radiation uniform across the detector. When bad pixels are identified in this manner, they are added to the detector's bad pixel map and are thereafter corrected in all applications and procedures. An additional method exists to identify and correct bad pixels as data is acquired. This method compares each pixel to a predetermined threshold and corrects each pixel that meets the criteria.

However, neither of these methods, identifying bad pixels by evaluating calibration images or comparing the pixel data as it is acquired to a predetermined value, will identify pixels that cause line artifacts when a detector is exposed to a non-uniform level of radiation and TFT leakage occurs. Thus, if an artifact is created only under certain circumstances, conventional methods may not identify susceptible pixels. As a consequence, it is desirable to be able to identify which detector elements may cause line artifacts when TFT leakage occurs. It is further desirable to correct the line artifact only after it has been determined that the line artifact exists, and also to correct only the pixels exhibiting the line artifact.

SUMMARY OF INVENTION

In accordance with at least one embodiment, a method is provided to identify detector elements, formed in rows and columns defining lines in a solid state X-ray detector, susceptible to causing line artifacts due to thin film transistor (TFT) leakage. A portion of the X-ray detector is covered by a radiation occluding material and the detector is exposed to a level of radiation sufficient to cause the TFT in a detector element in the exposed portion of the detector to conduct. An image is acquired representative of the amount of radiation detected. The detector elements are analyzed to determine whether line artifacts are present. In accordance with an alternative embodiment, during the analyzing step the acquired image is analyzed to determine whether line artifacts are present. Any data lines in the detector found to exhibit line artifacts are stored in the image processor. In accordance with an alternative embodiment, before analysis the resultant image is filtered to remove low frequency shading, and in another alternative embodiment, the covered portion of the detector is filtered to remove low frequency shading.

In accordance with at least one alternative embodiment, during the analyzing step a value is calculated for each line of the X-ray detector representing the radiation detected by detector elements in the covered portion of the line. In one embodiment, the line corresponds to a column of the detector, while in another embodiment the line corresponds to a row of the detector. The data values representative of at least the charge on the detector elements for each line along the covered portion of the line are summed and analyzed with respect to a predetermined threshold. In accordance with at least one embodiment, at least one data value includes a charge component from a detector element in the covered portion and a leakage component from a detector element in the exposed portion.

In accordance with at least one embodiment, a method is provided to correct line artifacts in a solid state X-ray detector caused by charge leakage of a TFT, a component of each detector element. The X-ray detector is exposed to radiation and an image is acquired representative of an amount of radiation detected by the detector elements. The data lines that were previously found to exhibit line artifacts are analyzed with respect to a predetermined threshold. The level of radiation exposure from the X-ray generator is then calculated with respect to a predetermined threshold and pixel correction is performed if it is required.

In accordance with at least one alternative embodiment, during the analyzing step it is determined for each line independently whether any data value exceeds or does not exceed the predetermined threshold. In one embodiment, the line corresponds to a column of the detector, while in another embodiment the line corresponds to a row of the detector. The data values are then analyzed to determine whether one or more data values first detected by the detector elements did not exceed the predetermined threshold.

The foregoing summary, as well as the following detailed description of the embodiments of the present invention, will be better understood when read in conjunction with the appended drawings. It should be understood, however, that the present invention is not limited to the arrangements and instrumentality shown in the attached drawings.

DETAILED DESCRIPTION

Figure 1:
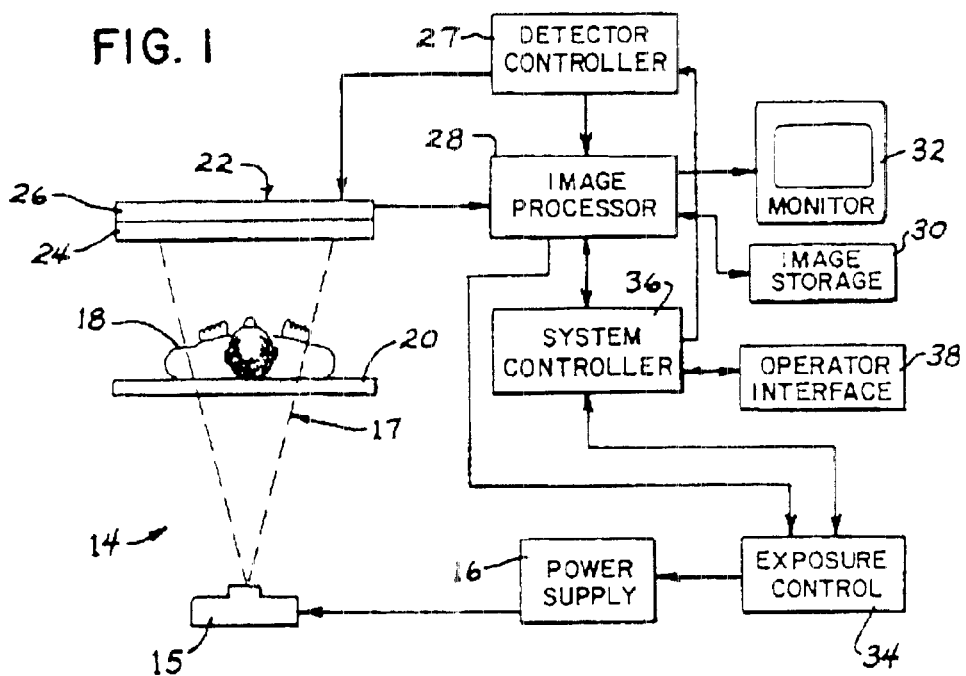
FIG. 1 illustrates a block diagram of an X-ray imaging system formed in accordance with an embodiment of a present invention.

With initial reference to FIG. 1, an X-ray apparatus 14 includes an X-ray tube 15 which, when excited by a power supply 16, emits an X-ray beam 17. As illustrated, the X-ray beam 17 is directed toward a patient 18 lying on an X-ray transmissive table 20. The portion of the beam 17 which is transmitted through the table 20 and the patient 18 impinges upon an X-ray detector designated 22. The X-ray detector 22 comprises a scintillator 24 that converts the X-ray photons to lower energy photons in the visible spectrum. Contiguous with the scintillator 24 is a photodetector array 26, which converts the light photons into an electrical signal. A detector controller 27 contains electronics for operating the detector array to acquire an image and to read out the signal from each photodetector element.

The output signal from the photodetector array 26 is coupled to an image processor 28 that includes circuitry for processing and enhancing the X-ray image signal. The processed image then is displayed on a video monitor 32 and may be archived in an image storage device 30. The image processor 28 additionally produces a brightness control signal which is applied to an exposure control circuit 34 to regulate the power supply 16 and thereby the X-ray exposure. The overall operation of the X-ray apparatus 14 is governed by a system controller 36 which receives commands from the X-ray technician via an operator interface panel 38.

Figure 2:
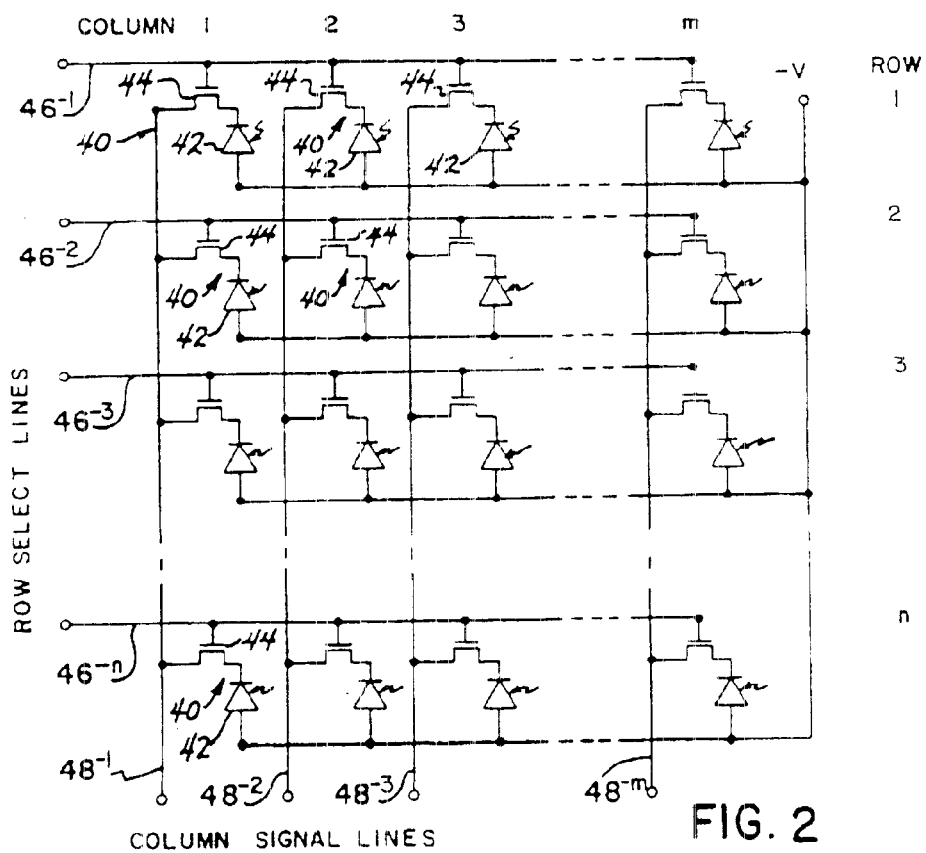
FIG. 2 illustrates a schematic diagram of the image detector array in the system of FIG. 1 formed in accordance with an embodiment of the present invention.

FIG. 2 illustrates the circuitry of the photodetector array 26, which is formed by a matrix of detector elements 40. The detector elements 40 are arranged on an amorphous silicon wafer in a conventional two-dimensional array of m columns and n rows, where m and n are integers. For example, a typical high resolution X-ray detector is a square array of 1,000 to 4,000 rows and columns of elements. Each detector element 40 includes a photo diode 42 and a thin film transistor (TFT) 44. The photo diodes 42 are fabricated from a large wafer area in order that the photo diode 42 will intercept a sizeable portion of the light produced by the scintillator 24. Each photo diode 42 also has a relatively large capacitance that allows it to store the electrical charge resulting from the photon excitation.

The cathode of the photo diodes 42 in each column of the array 26 is connected by the source-drain conduction path of the associated TFT 44 to a common column signal line ($48^{-1}$ through $48^{-m}$) for the column. For example the photo diodes 42 in column 1 are coupled to the first signal line 48. The anodes of the diodes in each row are connected in common to a source of a negative bias voltage (−V). The gate electrodes of the TFTs 44 in each row are connected to a common row select line ($46^{-1}$ through $46^{-n}$), such as line $46^{-1}$ for row 1. The row select lines and the column signal lines are coupled to the detector controller 27 and the column signal lines also are connected to the image processor 28.

In order to acquire an X-ray image using the detector 22 illustrated in FIG. 2, the apparatus 14 performs the following sequence of operations. Initially, the detector controller 27 connects all the column signal lines ($48^{-1}$ through $48^{-m}$) to ground; and applies a positive voltage ($V_{on}$) to all the row select lines ($46^{-1}$ through $46^{-n}$). The positive voltage applied to the row select lines turns on the TFT 44 in each detector element 40 placing a positive charge on the reverse biased photo diodes 42. Once the photo diodes 42 have been fully charged, the detector controller 27 applies a negative voltage ($-V_{off}$), which is more negative than the negative supply voltage ($-V$), to the row select lines (46$^{-1}$ through 46$^{-n}$). This negative biasing of the row select lines turns off the TFT 44 in each detector element 40.

Then the detector 22 is exposed to a pulse of X-ray photons produced in a conventional manner by the system exciting tube 15 to generate a beam 17 of X-ray photons. The X-ray photons are converted to lower energy photons by the scintillator 24. When these lower energy photons strike the photo diodes 42 in the detector 26, the electron-hole pairs are liberated and stored in the capacitance of the photo diode. The amount of charge stored in the given photo diode 42 depends upon the amount of lower energy photons which strikes it, which in turn depends upon the intensity of the X-ray energy that strikes the region of the scintillator 24 adjacent to the photo diode. Therefore, the amount of charge stored in the photo diode 42 in each detector element 40 is a function of the X-ray intensity striking the corresponding region of the X-ray detector 22.

After the termination of the X-ray exposure, the residual charge in each photo diode 42 is sensed. To do so, the column signal line (48$^{-1}$ through 48$^{-m}$) for each detector array column is simultaneously connected to separate sensing circuits in the image processor 28. Any of several types of sensing circuits can be incorporated into the image processor 28. For example, the sensing circuit can measure the voltage across the photo diode, and therefore the amount of charge stored in the photo diode. Alternatively, the sensing circuit can connect the associated column signal line (48$^{-1}$ through 48$^{-m}$) to a lower potential than the cathode of the photo diode and measure the amount of charge that flows to or from the photo diode.

For maximum image resolution, the photo diode charges are sensed a row at a time by the detector controller 27 sequentially applying the positive voltage ($V_{on}$) to each of the row select lines (46$^{-1}$ through 46$^{-n}$). When a row select line (46$^{-1}$ through 46$^{-n}$) is positively biased, the detector array TFTs 44 connected to that row select line (46$^{-1}$ through 46$^{-n}$) are turned on thereby coupling the associated photo diodes 42 in the selected row to their column signal lines (48$^{-1}$ through 48$^{-m}$).

Figure 3:
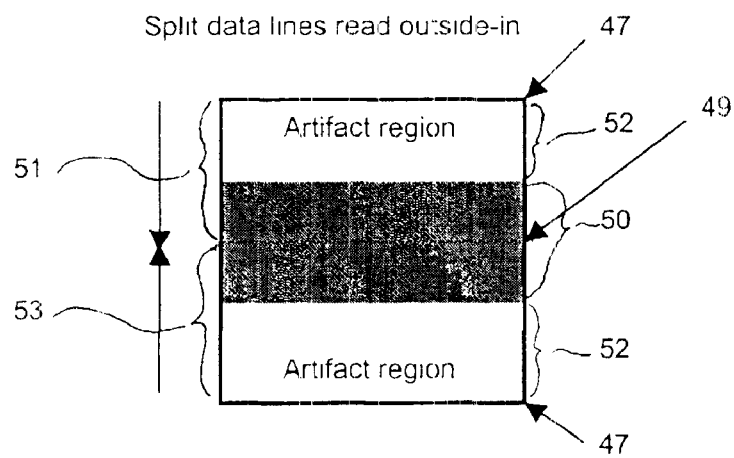
FIG. 3 illustrates a detector configuration formed in accordance with an embodiment of the present invention that may create image line artifacts.
Figure 4:
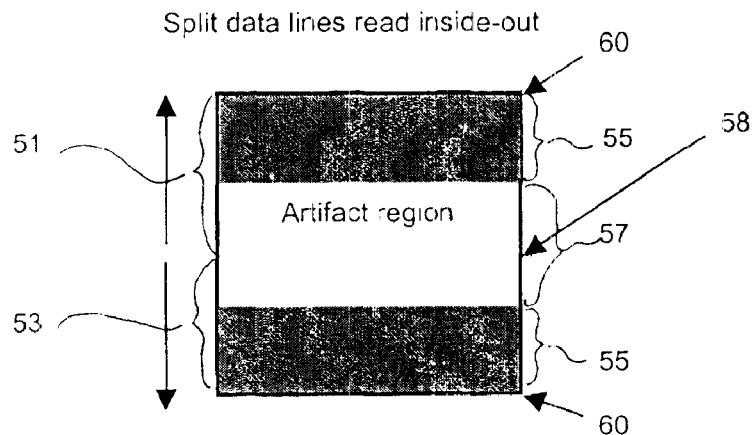
FIG. 4 illustrates an alternative detector configuration formed in accordance with an embodiment of the present invention that may create image line artifacts.

In order to decrease the amount of time required to read out the signal from each detector element 40 in the array, the rows of detector elements 40 can be divided into two groups and each group simultaneously read out. For example, as shown in FIG. 3 and FIG. 4, the detector elements 40 in the top half 51 of the array may be read out simultaneously with the detector elements 40 in the bottom half 53 in the array. It should be noted that this alternative embodiment of the photodetector array 26 requires twice the number of signal sensing circuits.

Figure 6:
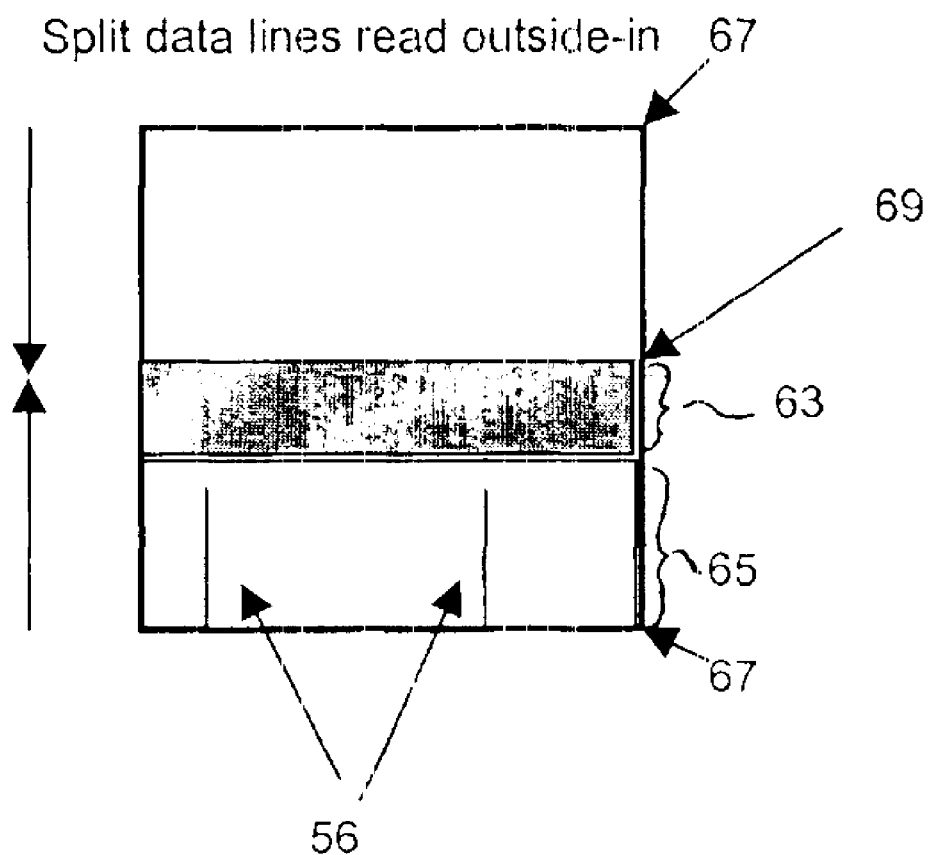
FIG. 6 illustrates an image containing line artifacts.

Under certain imaging conditions, line artifacts 56 may be created within the image. FIG. 6 shows an example of how line artifacts 56 may appear in the image. When a portion of the detector 22 is exposed to a high level of radiation (i.e. a level of radiation equal to or greater than the TFT 44 leakage threshold) such that the TFT 44 begin to conduct, the TFT 44 may leak signal onto a common column signal line (48$^{-1}$ through 48$^{-m}$). If a part of the common column signal line (48$^{-1}$ through 48$^{-m}$) is read in a portion of the detector 22 exposed to a low level of radiation (i.e. a level of radiation below the TFT 44 leakage threshold) before a part of the common column signal line (48$^{-1}$ through 48$^{-m}$) is read in a portion of the detector 22 exposed to a high level of radiation, the signals read from the common column signal line (48$^{-1}$ through 48$^{-m}$) may include a component due to leakage of the TFT 44 on the common column signal line (48$^{-1}$ through 48$^{-m}$) in addition to the direct X-ray signal.

For example, it may be assumed that the TFTs 44 in row 1 are exhibiting charge leakage onto the common column signal lines (48$^{-1}$ through 48$^{-m}$). Thus, when the detector controller 27 attempts to read out the detector elements 40 in row 3, the charge data values read out on common column lines (48$^{-1}$ to 48$^{-m}$) will include a charge component representative of the photon energy sensed by row 3 of the detector elements 40. However, in addition to the charge component, data values read out will also include a leakage component representative of the leakage charge from row 1 of the TFTs 44. The leakage component added to a charge component that is read out creates an artifact since the read out value does not correspond only to charge from the row of interest (row 3). The artifacts may appear along rows or columns (in lines) since a single leaking TFT 44 in a row (or column) may introduce a leakage charge or bias into each data value read from the row (or column).

Figure 5:
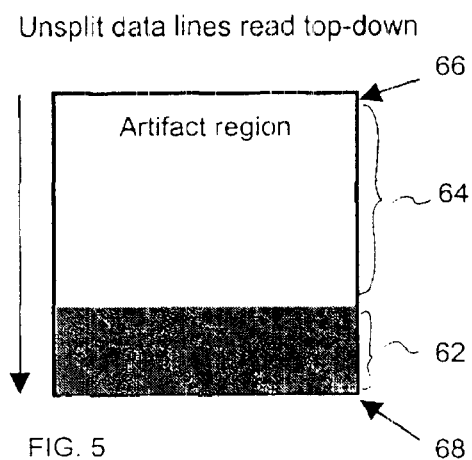
FIG. 5 illustrates a further alternative detector configuration formed in accordance with an embodiment of the present invention that may create image line artifacts.

If the magnitude of the TFT 44 leakage signal becomes large enough, it may lead to line artifacts 56. FIG. 3, FIG. 4, and FIG. 5 illustrate detectors 22 that may experience line artifacts 56 under given conditions. A portion of each detector 22 was exposed to a high level of radiation, while the remainder of the detector 22 was covered or was exposed to a low level of radiation. If the portion of the detector 22 exposed to the low level of radiation is read out first, the line artifact 56 may appear in the area exposed to the low level of radiation. Both FIG. 3 and FIG. 4 have split common row select lines (46$^{-1}$ through 46$^{-n}$), such that the detector elements 40 are divided into two groups, the top half 51 and the bottom half 53, and the top half 51 of the photodetector array 26 is read out simultaneously with the bottom half 53 of the photodetector array 26.

In FIG. 3, the center region 50 of the detector 22 was exposed to a high level of radiation, such that the signal was sufficient to cause the TFTs 44 to conduct. The edge regions 52 were not exposed to the high level of radiation, such as due to an intervening patient portion or other radiation occluding material. The circumstance may be created when imaging an object on one or more of the edge regions 52 that is not large enough to also cover the center region 50. The common row select lines (46$^{-1}$ through 46$^{-n}$) were then read from the outside edges 47, in the edge regions 52, towards the center of the detector 49, in the center region 50. Due to the exposure of center region 50 to the high level of radiation and the direction in which the detector elements 40 were read, line artifacts 56 may be created in the edge regions 52.

FIG. 4 illustrates another example of how line artifacts 56 may be created on a detector 22 with split common row select lines (46$^{-1}$ through 46$^{-n}$). The edge regions 55 of the detector 22 in FIG. 4 were exposed to a high level of radiation great enough to cause the TFTs 44 to conduct. The center region 57 was exposed to a lower level of radiation, as may occur when imaging an object in the center region 57 of the detector 22 of a size that does not extend to cover the edge regions 55 of the detector 22. The common row select lines (46$^{-1}$ through 46$^{-n}$) were then read from the center of the detector 58, in the center region 57, towards the outside edges 60 of the detector, in the edge regions 55. Because the edge regions 55 of the detector 22 were exposed to a high level of radiation and the direction the detector elements 40 were read was from the inside towards the outside, line artifacts 56 may be created in the center region 57.

Line artifacts 56 may also be created in a detector 22 with common row select lines (46$^{-1}$ through 46$^{-n}$) that are read consecutively from one end of the detector 22 to the other end. In FIG. 5, the bottom edge region 62 of the detector 22 was exposed to a high level of radiation, sufficient to cause the TFTs 44 to conduct. The top region 64 of the detector 22 received a low level of radiation, below the TFT 44 threshold. The circumstance may occur when imaging an object that covers a portion of the detector 22 fully at one end but not the other. The common row select lines ($46^{-1}$ through $46^{-n}$) were then read from the top of the detector 66, in the region that received a low level of radiation, to the bottom of the detector 68, in the region that received a high level of radiation. Because the top region 64 was read before the bottom edge region 62, line artifacts 56 may be created in the top region 64.

An example of how line artifacts 56 may appear on the X-ray image may be found in FIG. 6. The center area 63 of the detector 22 was exposed to a high level of radiation. Due to some form of radiation occluding material, the edge region 65 was exposed to a low level of radiation. The common row select lines ($46^{-1}$ through $46^{-n}$) were then read from the outside edge 67 toward the center of the detector 69. The detector 22 in FIG. 6 exhibits two line artifacts 56 in the edge region 65, the region exposed to a low level of radiation, along two of the column signal lines ($48^{-1}$ through $48^{-m}$). A detector 22 may have no line artifacts 56 or one or more line artifacts 56. An artifact may extend along only a portion of a column (or row) depending upon the location of the conducting TFTs 44 and the order in which data is read out from the detector 22.

In accordance with at least one embodiment, a method is provided to determine which data lines are susceptible to displaying line artifacts 56. The line artifacts 56 may occur if a portion or portions of the detector 22 were exposed to a level of radiation equal to or above the TFT 44 leakage threshold as illustrated in the center region 50 of FIG. 3 and the bottom edge region 62 of FIG. 5, and the remaining portion or portions of the detector 22 were exposed to a level of radiation below the TFT 44 leakage threshold as illustrated in the edge regions 52 of FIG. 3 and the top region 64 of FIG. 5. The method applies to detectors 22 that are read out one row at a time sequentially in one direction, as illustrated in FIG. 5, and detectors 22 where the rows of detector elements 40 are divided into two groups, as shown by the top half 51 and bottom half 53 in FIG. 3 and FIG. 4.

Figure 7:
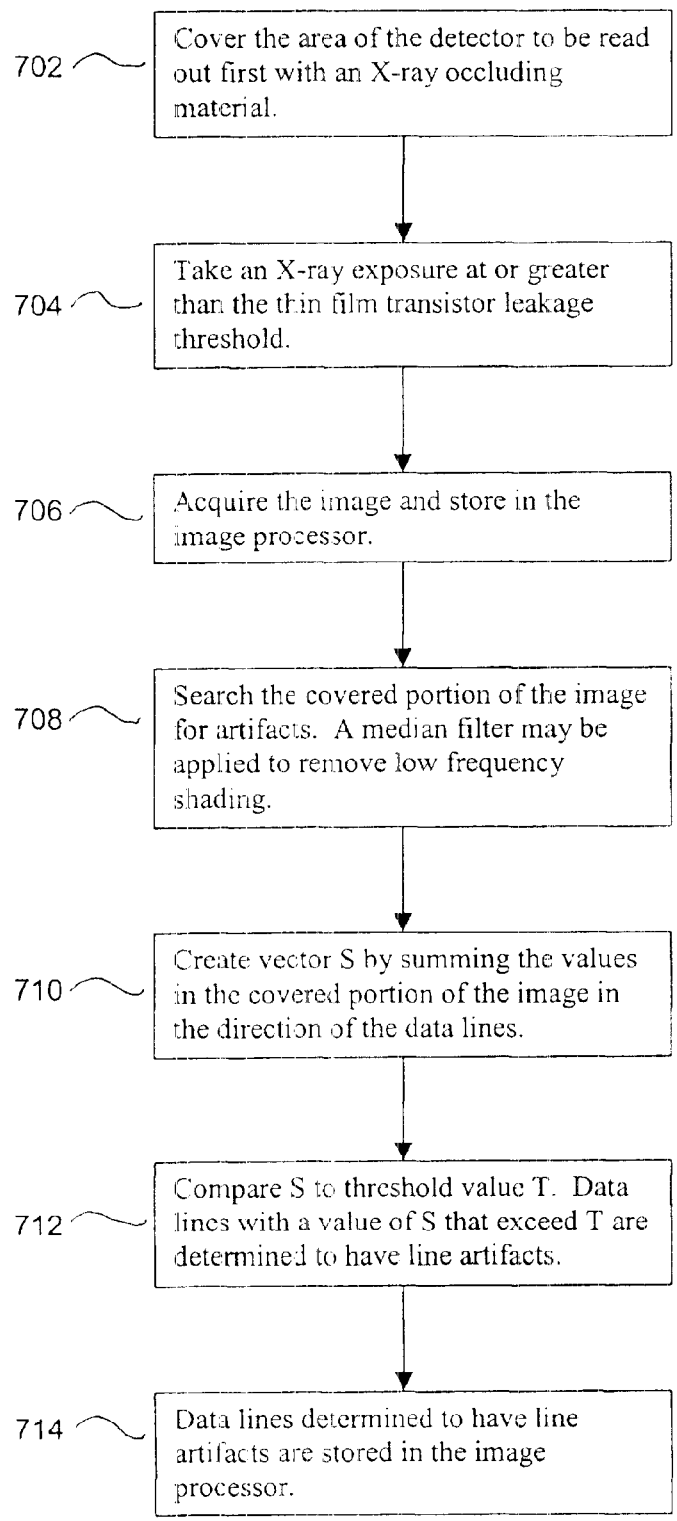
FIG. 7 illustrates a flow-chart of a process to identify data lines susceptible to line artifacts performed in accordance with an embodiment of the present invention.

FIG. 7 illustrates a flow-chart of a method for identifying data lines susceptible to line artifacts 56. As shown at block 702, in order to determine which data lines may exhibit line artifacts 56, the portion or portions of the detector 22 to be read out first, such as the edge regions 52 of FIG. 3, are covered by an X-ray occluding material (such as lead) to greatly diminish the amount of X-ray exposure. By way of example, rectangular blades from the X-ray tube collimator may be used to block X-rays. Alternatively, an X-ray opaque material may be placed close to the detector.

The next step, as illustrated at block 704 of FIG. 7, is to take a sufficiently high X-ray exposure, at or greater than the TFT 44 leakage threshold, in the uncovered region of the detector 22. Continuing to use FIG. 3 as an example, the center region 50 would be the uncovered detector region. The X-ray image is acquired by sequentially reading rows of detector elements 40 and storing the information on a computer for processing, block 706. The image shall be called X for the remainder of the discussion.

The edge regions 52 of the image X are searched for line artifacts 56 at block 708. It is normal for this image to have a low frequency shading as depicted in the edge region 65 of FIG. 6, in addition to line artifacts 56. In order to remove the low frequency shading, a median filter in the direction perpendicular to the data lines may be applied to create the following image:

Y(r,c)=X(r,c)−MedianFilter (X(r,c), N), where N is the width of the median filter, and may have the value of 5. The variables r and c indicate the row and column coordinates. If the data lines are in the column direction as indicated in the example in FIG. 6, the output of Median-Filter at each pixel X(r,c) is the median of the values [X(r, c−N/2) X(r, c−(N/2−1) . . . X(r, c) . . . X(r, c+(N/2−1) X(r, c+N/2].

The values in the covered region of image Y (edge region 52 of FIG. 3) are then summed in the direction of the data lines to create a vector S at block 710. If the data lines are in the column direction, S is given by:

S(c)=Sum_r(Y(r,c)), where Sum_r sums over all rows in the covered area. The line artifacts 56 are determined for those data lines for which S exceeds some threshold value T, block 712. The value of threshold T may be application specific. Methods for determining the value include perception studies with human observers in which line artifacts are added to images, and the threshold contrast level of detectability is determined. Alternatively, the sum may be divided by the number of rows exposed to high radiation for a given column.

It should be noted that the use of this median filter technique is just an example for extraction of the line artifacts 56. Other methods such as frequency analysis, background subtraction through low pass filtering, or similar may also yield appropriate results.

The identified data lines ($48^{-1}$ through $48^{-m}$) determined by the calibration method of FIG. 7 are stored on the X-ray image processor 28 so that clinical images may be corrected, block 714. In accordance with at least one embodiment, one of two methods may be used for line correction, namely a signal independent method and a signal dependent method. In the signal independent method, all data lines ($48^{-1}$ through $48^{-m}$) that have been identified as being susceptible to line artifacts 56 caused by TFT 44 leakage are corrected. Artifact correction may be achieved by correcting bad data lines ($48^{-1}$ through $48^{-m}$) in the digital detector 22, for example, by replacing all of the pixels on a line by the average of two neighboring lines. For example, if column 3 is identified to include line artifacts, column 3 may be replaced by the average of columns 2 and 4. In signal independent methods, the column 3 is replaced in every acquired image, independent of the particular application. In certain applications, the column 3 may not actually exhibit a line artifact. Notwithstanding a lack of line artifact, column 3 is replaced with the average of columns 2 and 4 anyway since column 3 was identified during calibration to be susceptible to charge leakage.

In the signal dependent method, lines are only corrected when the leakage threshold of a TFT 44 actually has been reached in a particular application and charge leakage has occurred. The method includes the steps shown in FIG. 8, which are applied to each line determined by the line identification procedure.

Figure 8:
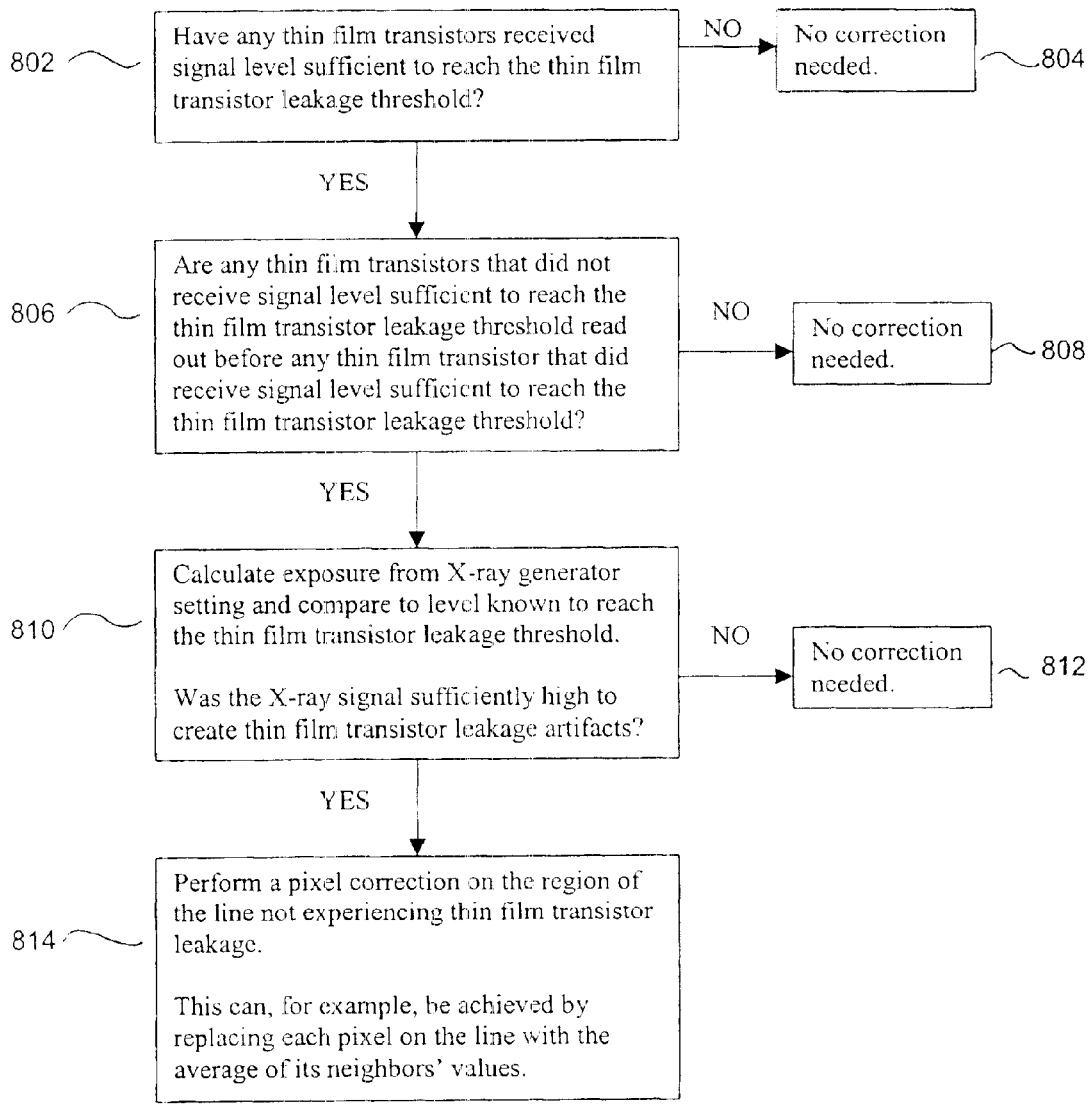
FIG. 8 illustrates a flow-chart of a process to correct line artifacts performed in accordance with an embodiment of the present invention.

At block 802 of FIG. 8 the method and apparatus inquires, "Have any thin film transistors received signal level sufficient to reach the thin film transistor leakage threshold?" The step at block 802 determines whether any portion of the detector received an amount of signal sufficient to cause TFT 44 leakage. If the answer is No, the TFT 44 leakage situation is not occurring. Control passes to block 804 of FIG. 8 the method and apparatus and no data line ($48^{-1}$ through $48^{-m}$)

correction is required. If the answer is Yes, more information is required to determine whether the TFT 44 leakage situation is occurring.

Next, at block 806 the method and apparatus inquires, "Are any thin film transistors that did not receive signal level sufficient to reach the thin film transistor leakage threshold read out before any thin film transistor that did receive signal level sufficient to reach the thin film transistor leakage threshold?" Referring back to FIG. 3, the edge region 52, which received a low level of radiation, is read out before the center region 50, which received a level of radiation sufficient to cause the TFTs 44 to conduct. In this example, the imaging conditions necessary to create the line artifacts 56 exist. If the answer to the block 806 is No, control passes to block 808 of FIG. 8 the method and apparatus and no data line ($48^{-1}$ through $48^{-m}$) correction is required. If the answer is Yes, continue to block 810.

At block 810 the method and apparatus inquires, "Calculate exposure from X-ray generator setting and compare to level known to reach the thin film transistor leakage threshold. Was the X-ray signal sufficiently high to create thin film transistor leakage artifacts?" If the answer to the block 810 is No, control passes to block 812 of FIG. 8 the method and apparatus and no data line ($48^{-1}$ through $48^{-m}$) correction is required. If it is determined that the X-ray signal was of a level great enough to reach the TFT 44 leakage threshold and cause TFT 44 leakage, continue to block 814 the method and apparatus.

At block 814 the method and apparatus, pixel correction will be performed on the region of the line not experiencing TFT 44 leakage. This correction may be achieved by replacing each pixel on the line with the average of its neighbors' values. It should be noted that other methods of pixel correction may also yield appropriate results.

Once the flow-chart has terminated at one of the blocks 804, 808, 812, or 814, the process of correcting possible line artifacts on the data line is complete. The blocks 802 through 814 are repeated for each data line determined by the line identification procedure.

While the invention has been described with reference to at least one embodiment, it will be understood by those skilled in the art that various changes may be made and equivalents may be substituted without departing from the scope of the invention. In addition, many modifications may be made to adapt a particular situation or material to the teachings of the invention without departing from its scope. Therefore, it is intended that the invention not be limited to the particular embodiment disclosed, but that the invention will include all embodiments falling within the scope of the appended claims.

What is claimed is:

1. A method of detecting line artifacts in a digital X-ray detector, having a matrix of detector elements formed in rows and columns defining lines of detector elements to be read out, the method comprising:

covering a portion of the X-ray detector with a radiation occluding material;

exposing the X-ray detector to radiation having a level sufficient to reach a predetermined threshold in an exposed portion of the X-ray detector not covered by the occluding material; and analyzing the detector elements in at least the covered portion of the X-ray detector with respect to the predetermined threshold to identify the lines of the detector elements containing the faulty detector elements in the exposed portion that leak charge.

2. The method of claim 1, further comprising:

acquiring an image representative of an amount of radiation detected by the detector elements in the covered portion and the exposed portion of the X-ray detector, wherein said analyzing step operates upon the acquired image.

3. The method of claim 2, further comprising:

filtering a portion of the image corresponding to the covered portion of the X-ray detector to remove low frequency shading.

4. The method of claim 1, further comprising:

filtering the covered portion of the X-ray detector to remove low frequency shading.

5. The method of claim 1, wherein the analyzing step further comprises:

calculating, for each line f the X-ray detector, a value representative of the radiation detected by the detector elements in the covered portion of a corresponding line.

6. The method of claim 5, wherein each said line corresponds to the column of the X-ray detector.

7. The method of claim 5, wherein each said line corresponds to the row of the X-ray detector.

8. The method of claim 1, wherein the analyzing step further comprises:

summing, for each said line independently of the X-ray detector, data values representative at least of a charge on the detector elements in the covered portion to provide a sum for each said line, the sums being analyzed with respect to the predetermined threshold.

9. The method of claim 8, wherein at least one said data value includes a bias component corresponding to leakage charge from at least one said detector element in the exposed portion of the X-ray detector.

10. The method of claim 1, wherein the analyzing step further comprises:

summing, for a series of detector elements aligned along the covered portion of one line, data values representative at least of the charge detected by the series of detector elements, the sum being analyzed with respect to the predetermined threshold.

11. The method of claim 1, further comprising:

obtaining data values corresponding to the detector elements, at least one said data value including a charge component from said detector element in the covered portion and a leakage component from said detector element in the exposed portion.

12. A method of correcting line artifacts in a digital X-ray detector, having a matrix of detector elements formed in rows and columns defining lines of detector elements to be read out, the method comprising:

exposing the X-ray detector to radiation from an X-ray source;

acquiring an image representative of an amount of radiation detected by the detector elements, said image including faulty detector elements;

analyzing the faulty detector elements with respect to a predetermined threshold;

calculating a level of radiation exposure from the X-ray source with respect to a predetermined threshold; and performing a pixel correction based upon the analysis of the faulty detector elements and the radiation exposure level.

13. The method of claim 12, wherein the analyzing step further comprises:

determining, for each said line independently of the X-ray detector, whether any data value detected by the detector elements exceeds the predetermined threshold.

14. The method of claim 13, wherein each said line corresponds to the column of the X-ray detector.

15. The method of claim 13, wherein each said line corresponds to the row of the X-ray detector.

16. The method of claim 13, wherein one or more said data values first detected by the detector elements did not exceed the predetermined threshold.

17. The method of claim 12, wherein the analyzing step further comprises:

determining, for each said line independently of the X-ray detector, which data values detected by the detector elements did not exceed the predetermined threshold.

18. The method of claim 12, wherein one or more data values are replaced by an average of the line data values on either side of the data value.

19. A method of correcting line artifacts in a digital X-ray detector, having a matrix of detector elements formed in rows and columns defining lines of detector elements to be read out, the method comprising:

exposing the X-ray detector to radiation from an X-ray source;

acquiring an image representative of an amount of radiation detected by the detector elements, said image including faulty detector elements;

analyzing the faulty detector elements with respect to a predetermined threshold;

determining, for each said line independently of the X-ray detector, whether any data value detected by the detector elements exceeds the predetermined threshold;

calculating a level of radiation exposure from the X-ray source with respect to the predetermined threshold; and performing a pixel correction based upon the analysis of the faulty detector elements and the radiation exposure level.

20. The method of claim 19, wherein one or more said data values first detected by the detector elements not exceed the predetermined threshold.

21. A method of detecting line artifacts in a digital X-ray detector, having a matrix of detector elements formed in rows and columns defining lines of the detector elements to be read out, the method comprising:

covering a portion of the X-ray detector with a radiation occluding material;

exposing the X-ray detector in an exposed portion of the X-ray detector not covered by the occluding material to radiation having a level at least as great as a TFT leakage threshold;

acquiring an image representative of an amount of radiation detected by the detector elements in the covered portion and the exposed portion of the X-ray detector, wherein said analyzing step operates upon the acquired image; and analyzing the detector elements in at least the covered portion of the X-ray detector with respect to a predetermined threshold to identify the lines of the detector elements containing the faulty detector elements in the exposed portion that leak charge.

22. The method of claim 21, further comprising:

filtering the covered portion of the X-ray detector to remove low frequency shading.

* * * * *